United States Patent [19]

Shields

[11] 4,061,607
[45] Dec. 6, 1977

[54] SOMATOSTATIN ANALOGS AND INTERMEDIATES THERETO

[75] Inventor: James E. Shields, Indianapolis, Ind.

[73] Assignee: Eli Lilly and Company, Indianapolis, Ind.

[21] Appl. No.: 709,465

[22] Filed: July 28, 1976

[51] Int. Cl.² .................... C08L 67/00; C07C 103/52
[52] U.S. Cl. ................................. 260/8; 260/112.5 S
[58] Field of Search .............................. 260/112.5 S, 8

[56] References Cited

PUBLICATIONS

J.A.C.S., (1974), pp. 2986–2992, vol. 96.

*Primary Examiner*—Delbert R. Phillips

*Attorney, Agent, or Firm*—William C. Martens, Jr.; Everet F. Smith

[57] ABSTRACT

The tetradecapeptides

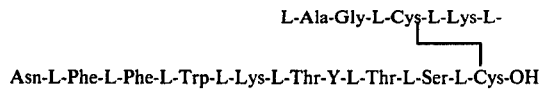

Asn-L-Phe-L-Phe-L-Trp-L-Lys-L-Thr-Y-L-Thr-L-Ser-L-Cys-OH in which Y is L-Cha, L-Leu, or D-Phe are described along with corresponding non-toxic pharmaceutically-acceptable acid addition salts as well as intermediates useful in the synthesis of the tetradecapeptides. These tetradecapeptides as well as their pharmaceutically-acceptable acid addition salts inhibit the release of growth hormone.

28 Claims, No Drawings

SOMATOSTATIN ANALOGS AND INTERMEDIATES THERETO

BACKGROUND AND SUMMARY OF THE INVENTION

This invention is directed to the tetradecapeptides

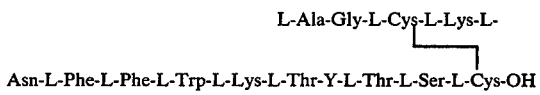

in which Y is L-Cha, L-Leu, or D-Phe as well as to their pharmaceutically acceptable acid addition salts and to intermediates produced during the synthesis of the tetradecapeptides.

Somatostatin (also known as somatotropin release inhibiting factor) is a tetradecapeptide of the formula

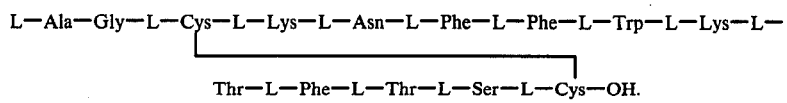

This tetradecapeptide was isolated from ovine hypothalamic extracts and was found to be active in inhibiting the secretion of growth hormone (GH), also known as somatotropin. In this regard, see P. Brazeau, W. Vale, R. Burgus, N. Ling, M. Butcher, J. Rivier, and R. Guillemin, Science, 179, 77 (1973).

The biologically active tetradecapeptides of this invention have the formula defined above and include the non-toxic acid addition salts thereof. Their structures differ from that of somatostatin by the presence of a D-phenylalanine residue, an L-cyclohexylalanine residue, or an L-leucine residue in position 11 in place of an L-phenylalanine residue. For convenience sake, the tetradecapeptides of this invention can be referred to as D-Phe[11]-somatostatin; L-Cha[11]-somatostatin; and L-Leu[11]-somatostatin.

Thus, this invention is directed to a compound selected from those of the formula

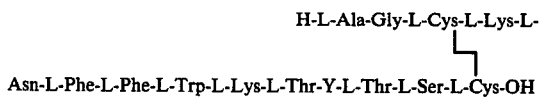

and their pharmaceutically-acceptable non-toxic acid addition salts, and R-L-Ala-Gly-L-Cys($R_1$)-L-Lys($R_2$)-L-Asn-L-Phe-L-Phe-L-Trp($R_5$)-L-Lys($R_2$)-L-Thr($R_3$)-Y-L-Thr($R_3$)-L-Ser($R_4$)-L-Cys($R_1$)-X; in which Y is D-PHe, L-Cha, or L-Leu;
R is hydrogen or an α-amino protecting group;
$R_1$ is hydrogen or a thio protecting group;
$R_2$ is hydrogen or an ε-amino protecting group;
$R_3$ and $R_4$ each are hydrogen or a hydroxy protecting group;
$R_5$ is hydrogen or formyl; and
X is hydroxy or

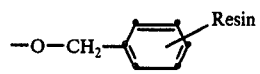

in which the resin is polystyrene; with the proviso that, when X is hydroxy, each of R, $R_1$, $R_2$, $R_3$, $R_4$, and $R_5$ is hydrogen, and, when X is

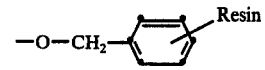

each of R, $R_1$, $R_2$, $R_3$, and $R_4$ is other than hydrogen.

DETAILED DESCRIPTION OF THE INVENTION

As indicated above, this invention in part is directed to compounds conveniently referred to as D-Phe[11]-somatostatin; L-Cha[11]-somatostastin; and L-Leu[11]-somatostatin, as well as to pharmaceutically-acceptable non-toxic acid addition salts of each.

Pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salts are those prepared from acetic acid. Any of the above salts are prepared by conventional methods.

Also contemplated as being within the scope of this invention are intermediates of the formula R-L-Ala-Gly-L-Cys($R_1$)-L-Lys($R_2$)-L-Asn-L-Phe-L-Phe-L-Trp($R_5$)-L-Lys($R_2$)-L-Thr($R_3$)-D-Phe-L-Thr($R_3$)-L-Ser($R_4$)-L-Cys($R_1$)-X; R-L-Ala-Gly-L-Cys($R_1$)-L-Lys($R_2$)-L-Asn-L-Phe-L-Phe-L-Trp($R_5$)-L-Lys($R_2$)-L-Thr($R_3$)-L-Cha-L-Thr($R_3$)-L-Ser($R_4$)-L-Cys($R_1$)-X; and R-L-Ala-Gly-L-Cys($R_1$)-L-Lys($R_2$)-L-Asn-L-Phe-L-Phe-L-Trp($R_5$)-L-Lys($R_2$)-L-Thr($R_3$)-L-Leu-L-Thr($R_3$)-L-Ser($R_4$)-L-Cys($R_1$)-X.

Preferred intermediates include the following:
H-L-Ala-Gly-L-Cys-L-Lys-L-Asn-L-Phe-L-Phe-L-Trp-L-Lys-L-Thr-D-Phe-L-Thr-L-Ser-L-Cys-OH;
H-L-Ala-Gly-L-Cys-L-Lys-L-Asn-L-Phe-L-Phe-L-Trp-L-Lys-L-Thr-L-Cha-L-Thr-L-Ser-L-Cys-OH;
H-L-Ala-Gly-L-Cys-L-Lys-L-Asn-L-Phe-L-Phe-L-Trp-L-Lys-L-Thr-L-Leu-L-Thr-L-Ser-L-Cys-OH;

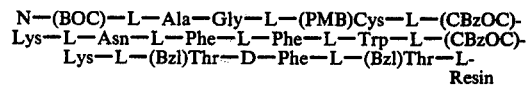

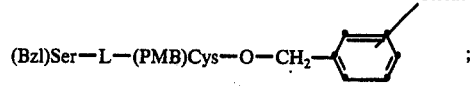

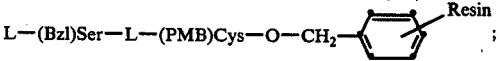

and

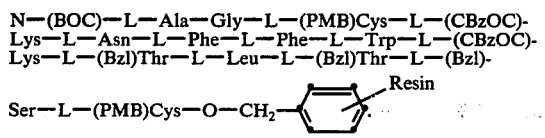

In the above formulas defining the intermediates, R represents either an α-amino hydrogen or an α-amino protecting group. The α-amino protecting groups contemplated for R are well recognized by those of ordinary skill in the peptide art. Many of these are detailed in the treatise *Protective Groups in Organic Chemistry*, M. F. W. McOmie, Editor, Plenum Press, New York, 1973, in Chapter 2, authored by J. W. Barton. Illustrative of such protecting groups are benzyloxycarbonyl, p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-methoxybenzyloxycarbonyl, p-nitrobenzyloxycarbonyl, t-butyloxycarbonyl (BOC), t-amyloxycarbonyl, 2-(p-biphenyl)isopropyloxycarbonyl (BpOC), adamatyloxycarbonyl, isopropyloxycarbonyl, cyclopentyloxycarbonyl, cyclohexyloxycarbonyl, cycloheptyloxycarbonyl, triphenylmethyl (trityl), p-toluenesulfonyl, and the like. Preferably, the α-amino protecting group defined by R is t-butyloxycarbonyl.

$R_1$ represents either the hydrogen of the sulfhydryl group of the cysteine ora protecting group for the sulfhydryl substituent. Illustrative suitable such protecting groups are p-methoxybenzyl, benzyl, p-tolyl, benzhydryl, acetamidomethyl, trityl, p-nitrobenzyl, t-butyl, isobutyloxymethyl, as well as any of a number of trityl derivatives. For additional groups, see, for example, Houben-Weyl, *Methodes der Organischen Chemie*, "Synthese von Peptiden", Vols. 15/1 and 15/2, (1974), Stuttgart, Germany. Preferably, the sulfhydryl protecting group defined by $R_1$ is p-methoxybenzyl.

$R_2$ represents either hydrogen on the ε-amino function of the lysine residue or a suitable ε-amino protecting group. Illustrative of such groups are the bulk of those mentioned hereinabove as being suitable for use as an α-amino protecting group. Included as typical such groups are benzyloxycarbonyl, t-butyloxycarbonyl, t-amyloxycarbonyl, cyclopentyloxycarbonyl, adamantyloxycarbonyl, p-methoxybenzyloxycarbonyl, p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-nitrobenzyloxycarbonyl, isopropyloxycarbonyl, cyclohexyloxycarbonyl, cycloheptyloxycarbonyl, p-toluenesulfonyl, and the like.

As will become apparent hereinafter, the method of preparation of the tetradecapeptides of this invention involves periodic cleavage of the α-amino protecting group from the terminal amino acid present on the peptide chain. Thus, the only limitation with respect to the identity of the ε-amino protecting group on the lysine residue is that it be such that it will not be cleaved under the conditions employed in selectively cleaving the α-amino protecting group. Appropriate selection of the α-amino and the ε-amino protecting groups is a matter well within the knowledge of a peptide chemist of ordinary skill in the art and depends upon the relative ease with which a particular protecting group can be cleaved. Thus, groups such as 2-(p-biphenylyl)isopropyloxycarbonyl (BpOC) and trityl are very labile and can be cleaved even in the presence of mild acid. A moderately strong acid, such as hydrochloric acid, trifluoroacetic acid, or boron trifluoride in acetic acid, is required to cleave other groups such as t-butyloxycarbonyl, t-amyloxycarbonyl, adamantyloxycarbonyl, and p-methoxybenzyloxycarbonyl. Even stronger acid conditions are required to effect cleavage of other protecting groups such as benzyloxycarbonyl, halobenzyloxycarbonyl, p-nitrobenzyloxycarbonyl, cycloalkyloxycarbonyl, and isopropyloxycarbonyl. Cleavage of these latter groups requires drastic acid conditions such as the use of hydrogen bromide, hydrogen fluoride, or boron trifluoroacetate in trifluoroacetic acid. Of course, any of the more labile groups will also be cleaved under the stronger acid conditions. Appropriate selection of the amino protecting groups thus will include the use of a group at the α-amino function which is more labile than that employed as the ε-amino protecting group coupled with cleavage conditions designed to selectively remove only the α-amino function. In this context, $R_2$ preferably is cyclopentyloxycarbonyl, and, in conjunction therewith, the α-amino protecting group of choice for use in each of the amino acids which is added to the peptide chain preferably is t-butyloxycarbonyl.

The groups $R_3$ and $R_4$ represent the hydroxyl hydrogen or a protecting group for the alcoholic hydroxyl of threonine and serine, respectively. Typical such protecting groups are, for example, $C_1$-$C_4$ alkyl, such as methyl, ethyl, t-butyl, and the like; benzyl; substituted benzyl, such as p-methoxybenzyl, p-nitrobenzyl, p-chlorobenzyl, o-chlorobenzyl, and the like; $C_1$-$C_3$ alkanoyl, such as formyl, acetyl, and propionyl; triphenylmethyl (trityl); and the like. Preferably, when $R_3$ and $R_4$ are protecting groups, the protecting group of choice in both instances is benzyl.

The group $R_5$ represents either hydrogen or formyl and defines the moiety >$NR_5$ of the tryptophan residue. The formyl serves as a protecting group. The use of such a protecting group is optional and, therefore, $R_5$ properly can by hydrogen (N-unprotected) or formyl (N-protected).

The group X relates to the carboxyl terminal of the tetradecapeptide chain; it can be hydroxyl, in which case a free carboxyl group is defined. In addition, X represents the solid resin support to which the carboxyl terminal moiety of the peptide is linked during its synthesis. This solid resin is represented by the formula

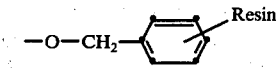

In any of the above, when X represents hydroxyl, each of R, $R_1$, $R_2$, $R_3$, $R_4$, and $R_5$ is hydrogen. When X represents the solid resin support, each of R, $R_1$, $R_2$, $R_3$, and $R_4$ is a protecting group.

The following abbreviations, most of which are well known and commonly used in the art, are employed herein:

Ala - Alanine
Asn - Asparagine
Cha - Cyclohexylalanine
Cys - Cysteine
Gly - Glycine
Lys - Lysine
Phe - Phenylalanine
Ser - Serine
Thr - Threonine Trp - Tryptophan
DCC - N,N'-Dicyclohexylcarbodiimide
DMF - N,N-Dimethylformamide
BOC - t-Butyloxycarbonyl
PMB - p-Methoxybenzyl
CBzOC - o-Chlorobenzyloxycarbonyl
CPOC - Cyclopentyloxycarbonyl
Bzl - Benzyl
For - Formyl
BpOC - 2-(p-biphenylyl)isopropyloxycarbonyl Although the selection of the particular protecting groups to be employed in preparing the compounds of this invention remains a matter well within the ordinary skill of a synthetic peptide chemist, it is well to recognize that the proper selection of the protecting groups is dependent upon the particular succeeding reactions which must be carried out. Thus, the protecting group of choice must be one which is stable both to the reagents and under the conditions employed in the succeeding steps of the reaction sequence. For example, as already discussed to some degree hereinabove, the particular protecting group which is employed must be one which remains intact under the conditions which are employed for cleaving the α-amino protecting group of the terminal amino acid residue of the peptide fragment in preparation for the coupling of the next succeeding amino acid fragment to the peptide chain. It is also important to select, as a protecting group, one which will remain intact during the building of the peptide chain and which will be readily removable upon completion of the synthesis of the desired tetradecapeptide product. All of these matters are well within the knowledge and understanding of a peptide chemist of ordinary skill in the art.

As is evident from the above discussion, the tetradecapeptide of this invention can be prepared by solid phase synthesis. This synthesis involves a sequential building of the peptide chain beginning at the C-terminal end of the peptide. Specifically, cysteine first is linked at its carboxyl function to the resin by reaction of an amino-protected, S-protected cysteine with a chloromethylated resin or a hydroxymethyl resin. Preparation of a hydroxymethyl resin is described by Bodanszky et al., *Chem. Ind.* (London), 38 1597–98 (1966). The chloromethylated resin is commercially available from Lab Systems, Inc., San Mateo, Calif.

In accomplishing linkage of the C-terminal cysteine to the resin, the protected cysteine first is converted to its cesium salt. This salt then is reacted with the resin in accordance with the method described by B.F. Gisin, *Helv. Chim. Acta*, 56, 1476 (1973). Alternatively, the cysteine can be linked to the resin by activation of the carboxyl function of the cysteine molecule by application of readily recognized techniques. For example, the cysteine can be reacted with the resin in the presence of a carboxyl group activating compound such as N,N'-dicyclohexylcarbodiimide (DCC).

Once the free carboxyl cysteine has been appropriately linked to the resin support, the remainder of the peptide building sequence involves the step-wise addition of each amino acid to the N-terminal portion of the peptide chain. Necessarily, therefore, the particular sequence which is involved comprises a cleavage of the α-amino protecting group from the amino acid which represents the N-terminal portion of the peptide fragment followed by coupling of the next succeeding amino acid residue to the now free and reactive N-terminal amino acid. Cleavage of the α-amino protecting group can be effected in the presence of an acid such as hydrobromic acid, hydrochloric acid, trifluoroacetic acid, p-toluenesulfonic acid, benzenesulfonic acid, naphthalenesulfonic acid, acetic acid, and the like, with formation of the respective acid addition salt product. Another method which is available for accomplishing cleavage of the amino protecting group involves the use of boron trifluoride. For example, boron trifluoride diethyl etherate in glacial acetic acid will convert the amino-protected peptide fragment to a $BF_3$ complex which then can be converted to the deblocked peptide fragment by treatment with a base such as aqueous potassium bicarbonate. Any of these methods can be employed as long as it is recognized that the method of choice must be one which accomplishes cleavage of the N-terminal α-amino protecting group without disruption of any other protecting groups present on the peptide chain. In this regard, it is preferred that the cleavage of the N-terminal protecting group be accomplished using trifluoroacetic acid. Generally, the cleavage will be carried out at a temperature from about 0° C. to about room temperature.

Once the N-terminal cleavage has been effected, the product which results normally will be in the form of the acid addition salt of the acid which has been employed to accomplish the cleavage of the protecting group. The product then can be converted to the free terminal amino compound by treatment with a mild base, typically a tertiary amine such as pyridine, triethylamine, or the like.

The peptide chain then is ready for reaction with the next succeeding amino acid. This can be accomplished by employing any of several recognized techniques. In order to achieve coupling of the next-succeeding amino acid to the N-terminal peptide chain, an amino acid which has a free carboxyl but which is suitably protected at the α-amino function as well as at any other active moiety is employed. The amino acid then is subjected to conditions which will render the carboxyl function active to the coupling reaction. One such activation technique which can be employed in the synthesis involves the conversion of the amino acid to a mixed anhydride. Thereby, the free carboxyl function of the amino acid is activated by reaction with another acid, typically a carbonic acid in the form of its acid chloride. Examples of such acid chlorides which can be used to form the appropriate mixed anhydrides are ethyl chloroformate, phenyl chloroformate, sec-butyl chloroformate, isobutyl chloroformate, pivaloyl chloride, and the like.

Another method of activating the carboxyl function of the amino acid to achieve coupling is by conversion of the amino acid to its active ester derivative. Examples of such active esters are, for example, a 2,4,5-trichlorophenyl ester, a pentachlorophenyl ester, a p-nitrophenyl ester, an ester formed from 1-hydroxybenzotriazole, and an ester formed from N-hydroxysuccinimide. Another method for effecting coupling of the C-terminal amino acid to the peptide fragment involves carrying out the coupling reaction in the presence of at least an equimolar quantity of N,N'-dicyclohexylcarbodiimide (DCC). This latter method is preferred for preparing the tetradecapeptide of this invention.

Once the desired amino acid sequence has been prepared, the resulting peptide can be removed from the resin support. This is accomplished by treatment of the protected resin-supported tetradecapeptide with hydrogen fluoride. Treatment with hydrogen fluoride cleaves the peptide from the resin; in addition, however, it cleaves all remaining protecting groups present on the reactive moieties located on the peptide chain as well as the α-amino protecting group present at N-terminal amino acid. When hydrogen fluoride is employed to effect the cleavage of the peptide from the resin as well as removal of the protecting groups, it is preferred that the reaction be carried out in the presence of anisole. The presence of anisole has been found to inhibit the potential alkylation of certain amino acid residues present in the peptide chain. In addition, it is preferred that the cleavage be carried out in the presence of ethyl mercaptan. The ethyl mercaptan serves to protect the indole ring of the tryptophan residue and, furthermore, facilitates conversion of the blocked cysteines to their thiol forms. Also, when $R_5$ is formyl, the presence of ethyl mercaptan facilitates hydrogen fluoride cleavage of the formyl group.

Once the cleavage reaction has been accomplished, the product which is obtained is a straight-chain peptide containing 14 amino acid residues. In order to obtain the final product of this invention, it is necessary to treat the straight-chain tetradecapeptide under conditions which will effect its oxidation by converting the two sulfhydryl groups present in the molecule, one at each cysteinyl moiety, to a disulfide bridge. This can be accomplished by treating a dilute solution of the linear tetradecapeptide with any of a variety of oxidizing agents including, for example, iodine, potassium ferricyanide, and the like. Air also can be employed as oxidizing agent, the pH of the mixture generally being from about 2.5 to about 9.0, and preferably from about 7.0 to about 7.6. When air is used as oxidizing agent, the concentration of the peptide solution generally is not greater than about 0.4 mg. of the peptide per milliliter of solution, and usually is about 50 μg./ml.

The compounds of this invention having the disulfide linkage may be administered to warm-blooded mammals, including humans, by any of several methods, including orally, sublingually, subcutaneously, intramuscularly, intravenously, and the like. Each of these compounds is active, although not necessarily to an equivalent degree, in inhibiting the release of growth hormone. This inhibitory effect is beneficial in those instances in which the host being treated requires a therapeutic treatment for excess secretion of somatotropin, such secretion being associated with adverse conditions such as juvenile diabetes and acromegaly. L-Leu[11]-somatostain also exhibits an inhibitory effect upon the pancreatic secretion of insulin. Preferably, the dose range for sublingual or oral administration is about 1 mg. to about 100 mg./kg. of body weight per day. Generally, the dose range for intravenous, subcutaneous, or intramuscular administration is from about 10 μg. to about 1 mg/kg. of body weight per day, and, preferably, is from about 50 μg. to about 100 μg./kg. of body weight per day. It is evident that the dose range will vary widely depending upon the particular condition which is being treated as well as the severity of the condition.

It is also possible to administer the compounds of this invention in the form of tablets containing other inocuous ingredients. Inert diluents or carriers, for example, magnesium carbonate or lactose, can be used together with conventional disintegrating agents, for example, maize starch and alginic acid, and lubricating agents, for example, magnesium stearate. Typically, the amount of carrier or diluent will range from about 5 to about 95 percent of the final composition, and preferably from about 50 to about 85 percent of the final composition. Suitable flavoring agents also can be employed in the final preparation rendering the composition more palatable for administration.

When the compounds of this invention are to be administered intravenously, suitable carriers may be employed, such as, for example, isotonic saline, phosphate buffer solutions, and the like.

The following examples are illustrative of the preparation of compounds of this invention.

EXAMPLE 1

N-t-BUTYLOXYCARBONYL-L-CYSTEINYL(S-p-METHOXYBENZYL) METHYLATED POLYSTYRENE RESIN

To 51.0 g. of chloromethylated polystyrene resin (Lab Systems, Inc., 0.75 mmoles/gram) suspended in 500 ml. of N,N-dimethylformamide (DMF) were added 11.95 grams (25.25 mmoles) of the cesium salt of N-t-butyloxycarbonyl-(S-p-methoxybenzyl)cysteine. The mixture was stirred at room temperature for five days. The resin then was filtered and was washed successively twice with DMF, three times with a mixture of 90 percent DMF and 10 percent water, three times with 95% ethanol, and three times with DMF. To the resin suspended in 500 ml. of DMF were added a solution of 10.5 grams of cesium acetate. The mixture was stirred for seven days at room temperature. The resin then was filtered and was washed successively, twice with DMF, three times with a mixture of 90 percent DMF and 10 percent water, three times with 95% ethanol three times with methylene chloride, and three times with 95 percent ethanol. The resin then was dried in vacuo at 40° C. to obtain the title product. An amino acid analysis showed 0.258 mmoles of Cys per gram resin. The cysteine was determined as cysteic acid from an acid hydrolysis carried out using a 1:1 mixture of dioxane and conc. hydrochloric acid to which a small amount of dimethyl sulfoxide was added.

Example 2

N-t-BUTYLOXYCARBONYL-L-ALANYL-GLYCYL-L-(S-p-METHOXYBENZYL)CYSTEINYL-L-(Nε-o-CHLOROBENZYLOXYCARBONYL)LYSYL-L-ASPARAGINYL-L-PHENYLALANYL-L-PHENYLALANYL-L-TRYPTOPHYL-L-(Nε-o-CHLOROBENZYLOXYCARBONYL)LYSYL-L-(O-BENZYL)THREONYL-D-PHENYLALANYL-L-(O-BENZYL)THREONYL-L-(O-BENZYL)SERYL-L-(S-p-METHOXYBENZYL)CYSTEINYL METHYLATED POLYSTYRENE RESIN

The product from Example 1 (5.0 grams) was placed in the reaction vessel of a Beckman 990 automatic peptide synthesizer, and the remaining 13 amino acids were added employing the automatic synthesizer. The amino acids which were employed as well as the sequence of their employment is as follows: (1) N-t-butyloxycarbonyl-(O-benzyl)-L-serine; (2) N-t-butyloxycarbonyl-(O-benzyl)-L-threonine; (3) N-t-butyloxycarbonyl-D-phenylalanine; (4) N-t-butyloxycarbonyl-(O-benzyl)-L-threonine; (5) Nα-t-butyloxycarbonyl-Nε-o-chlorobenzyloxycarbonyl-L-lysine; (6) Nα-t-butyloxycarbonyl-L-tryptophan; (7) N-t-butyloxycarbonyl-L-phenylalanine; (8) N-t-butyloxycarbonyl-L-phenylalanine; (9) N-t-butyloxycarbonyl-L-asparagine, p-nitrophenyl ester; (10) Nα-t-butyloxycarbonyl-Nε-o-chlorobenzyloxycarbonyl-L-lysine; (11) N-t-butyloxycarbonyl-(S-p-methoxybenzyl)-L-cysteine; (12) N-t-butyloxycarbonyl-glycine; and (13) N-t-butyloxycarbonyl-L-alanine. The sequence of deprotection, neutralization, coupling, and recoupling for the introduction of each amino acid into the peptide is as follows: (1) three washes (10 ml./gram resin) of three minutes each with chloroform; (2) removal of BOC group by treatment twice for twenty minutes each with 10 ml./gram resin of a mixture of 28.8 percent trifluoroacetic acid, 65.4 percent chloroform, and 5.8 percent triethylsilane; (3) two washes (10 ml./gram resin) of three minutes each with chloroform; (4) one wash (10 ml./gram resin) of three minutes with methylene chloride; (5) three washes (10 ml./gram resin) of three minutes each with a mixture of 90 percent t-butyl alcohol and 10 percent t-amyl alcohol; (6) three washes (10 ml./gram resin) of three minutes each with methylene chloride; (7) neutralization by three treatments of three minutes each with 10 ml./gram resin of 3 percent triethylamine in methylene chloride; (8) three washes (10 ml./gram resin) of three minutes each with methylene chloride; (9) three washes (10 ml./gram resin) of three minutes each with a mixture of 90 percent t-butyl alcohol and 10 percent t-amyl alcohol; (10) three washes (10 ml./gram resin) of 3 minutes each with methylene chloride; (11) addition of 1.0 mmole/gram resin of the protected amino acid and 1.0 mmole/gram resin of N,N'-dicyclohexylcarbodiimide (DCC) in 10 ml./gram resin of methylene chloride followed by mixing for 120 minutes; (12) three washes (10 ml./gram resin) of three minutes each with methylene chloride; (13) three washes (10 ml./gram resin) of three minutes each with a mixture of 90 percent t-butyl alcohol and 10 percent t-amyl alcohol; (14) three washes (10 ml./gram resin) of three minutes each with methylene chloride; (15) neutralization by three treatments of three minutes each with 10 ml./gram resin of 3 percent triethylamine in methylene chloride; (16) three washes (10 ml./gram resin) of three minutes each with methylene chloride; (17) three washes (10 ml./gram resin) of three minutes each with a mixture of 90 percent t-butyl alcohol and 10 percent t-amyl alcohol; (18) three washes (10 ml./gram resin) of three minutes each with methylene chloride; (19) three washes (10 ml./gram resin) of three minutes each with DMF; (20) addition of 1.0 mmole/gram resin of the protected amino acid and 1.0 mmole/gram resin of N,N'-dicyclohexylcarbodiimide (DCC) in 10 ml./gram resin of a 1:1 mixture of DMF and methylene chloride followed by mixing for 120 minutes; (21) three washes (10 ml./gram resin) of three minutes each with DMF; (22) three washes (10 ml./gram resin) of three minutes each with methylene chloride; (23) three washes (10 ml./gram resin) of three minutes each with a mixture of 90 percent t-butyl alcohol and 10 percent t-amyl alcohol; (24) three washes (10 mg./gram resin) of three minutes each with methylene chloride; (25) neutralization by three treatments of three minutes each with 10 ml./gram resin of 3 percent triethylamine in methylene chloride; (26) three washes (10 mg./gram resin) of three minutes each with methylene chloride; (27) three washes (10 ml./gram resin) of three minutes each with a mixture of 90 percent t-butyl alcohol and 10 percent t-amyl alcohol; and (28) three washes (10 mg./gram resin) of three minutes each with methylene chloride.

The above treatment sequence was employed for addition of each of the amino acids with the exception of the asparagine residue. This residue was incorporated via its p-nitrophenyl active ester. In doing so, Step (11) above was modified to the following 3-step sequence: (a) three washes (10 ml./gram resin) of three minutes each with DMF; (b) addition of 1.0 mmole/gram resin of the p-nitrophenyl ester of N-t-butyloxycarbonyl-L-asparagine in 10 ml./gram resin of a 1:3 mixture of DMF and methylene chloride followed by mixing for 720 minutes; and (c) three washes (10 ml./gram resin) of three minutes each with DMF. Also, Step (20) above was modified to the use of a 3:1 mixture of DMF and methylene chloride instead of the 1:1 mixture.

The finished peptide-resin was dried in vacuo. A portion of the product was hydrolyzed by refluxing for 21 hours in a mixture of hydrochloric acid and dioxane. Amino acid analysis of the resulting product gave the following results, lysine being employed as standard: Asn, 1.12; 2Thr, 2.16; Ser, 1.08; Gly, 1.08; Ala, 1.14; 3Phe, 3.18; 2Lys, 2.00, Trp, 0.60. Tryptophan was determined by hydrolysis in the presence of thioglycolic acid. Cysteine was not determined since it is destroyed by the method of analysis.

EXAMPLE 3

L-ALANYL-GLYCYL-L-CYSTEINYL-L-LYSYL-L-ASPARAGINYL-L-PHENYLALANYL-L-PHE-NYL-ALANYL-L-TRYPTOPHYL-L-LYSYL-L-THREONYL-D-PHENYLALANYL-L-THREO-NYL-L-SERYL-L-CYSTEINE

To a mixture of 10 ml. of anisole and 10 ml. of ethyl mercaptan were added 2.708 grams (at substitution level of 0.155 mmoles/gram) of the protected tetradecapeptide-resin of Example 2. The mixture was cooled in liquid nitrogen, and 44 ml. of liquid hydrogen fluoride were added by distillation. The resulting mixture was allowed to warm to 0° C. and was stirred for 1.5 hours. The hydrogen fluoride then was removed by distillation, and ether was added to the remaining mixture. The resulting solid material was collected by filtration and washed with ether. The product was dried, and the deprotected tetradecapeptide was extracted from the resin mixture using degassed 1M acetic acid and a small amount of glacial acetic acid. The acetic acid solution then was immediately lyophilized to dryness in the dark. The resulting slightly yellow solid was suspended in a mixture of 12 ml. of degassed 0.2M acetic acid and 4 ml. of glacial acetic acid. The resulting suspension was filtered, and the filtrate was absorbed on a Sephadex G-25 F column. The chromatographic conditions were: solvent, degassed 0.2M acetic acid; column size, 7.5 × 150 cm.; temperature, 26° C.; flow rate, 668 ml./hour; fraction volume, 23.4 ml.

Absorbance at 280 mµ of each fraction plotted versus fraction number indicated one large peak with a shoulder on each side. A collection of three sets of fractions was made. The fractions which were combined and their effluent volumes are as follows:

Fractions 115-213 (2668-4984 ml.)
Fractions 214-230 (4985-5382 ml.)
Fractions 231-320 (5383-7488 ml.)

UV spectroscopy indicated that the second fraction contained the best product and that 123.7 mg. of the product were present. An Ellman titration of an aliquot indicated a free sulfhydryl content of 63% of theoretical.

EXAMPLE 4

OXIDATION TO D-Phe[11]-SOMATOSTATIN

The solution of the reduced D-Phe[11]-somatostatin for Example 3 was diluted with 0.2M acetic acid and distilled water to achieve a concentration of 50 μg./ml. Concentrated ammonium hydroxide was added to adjust the pH of the mixture to 6.9. The solution was stirred at room temperature for 90 hours after which an Ellman titration indicated that oxidation was complete.

The mixture was concentrated in vacuo to a viscous suspension. The suspension was dissolved in 14 ml. of 50% acetic acid and then was desalted in 50% acetic acid on a Sephadex G-25 F column. The chromatographic conditions were as follows: solvent, degassed 50% acetic acid; column size, 5.0 × 90 cm.; temperature, 26° C.; flow rate, 298 ml./hour; fraction volume, 17.4 ml.

Absorbance at 280 mμ for each fraction plotted versus fraction number indicated two large peaks. The first peak represented the aggregated forms of the product, and the second peak represented monomeric product. The material represented by the second peak was collected and lyophilized to dryness. The resulting white solid was dissolved in 6 ml. of degassed 0.2M acetic acid and was absorbed on a Sephadex G-25 F column. Chromatographic conditions were: solvent, degassed 0.2M acetic acid; column size, 5.0 × 150 cm.; temperature, 26° C.; flow rate, 483 ml./hour; fraction volume, 16.1 ml.

Absorbance at 280 mμ for each fraction plotted versus fraction number showed a product peak with sloping shoulders. UV spectroscopy indicated that the main part of the peak was good product. Fractions 165-182 (effluent volumes of 2640-2930 ml.) were combined and lyophilized to dryness to obtain 56.2 mg. of the desired product.

Optical rotation $[\alpha]_D^{26} = -40.7°$ (1 percent acetic acid).

Amino acid analysis: Ala, 1.0; Gly, 1.02; 2Cys, 1.95; 2Lys, 1.97; Asn, 1.05; 2Phe + D-Phe, 2.84; Trp, 0.85; 2Thr, 1.85; Ser. 0.80.

The above results are expressed as ratios to one-half the sum of glycine and alanine. Cysteine was determined as cysteic acid from hydrolysis in the presence of dimethyl sulfoxide; tryptophan was determined from hydrolysis in the presence of thioglycolic acid; serine was not corrected for losses during hydrolysis.

EXAMPLE 5

N-t-BUTYLOXYCARBONYL-L-ALANYL-GLYCYL-L-(S-p-METHOXYBENZYL)CYSTEINYL-L-(N$^\epsilon$-o-CHLOROBENZYLOXYCARBONYL)LYSYL-L-ASPARAGINYL-L-PHENYLALANYL-L-PHENYLALANYL-L-(FORMYL)TRYPTOPHYL-L-(N$^\epsilon$-o-CHLOROBENZYLOXYCARBONYL)LYSYL-L-(O-BENZYL)THREONYL-L-CYCLOHEXYLALANYL-L-(O-BENZYL)THREONYL-L-(O-BENZYL)-SERYL-L-(S-p-METHOXYBENZYL)-CYSTEINYL METHYLATED POLYSTYRENE RESIN This compound was prepared by a method similar to that described in Example 2 and using 3.5 grams of the product from Example 1 as starting material. The Beckman 990 automatic peptide synthesizer was used for the entire sequence. N-t-Butyloxycarbonyl-L-cyclohexylalanine was used in place of N-t-butyloxycarbonyl-D-phenylalanine, and N$^\epsilon$-t-butyloxycarbonyl-(N-formyl)-L-tryptophan was used in place of N$^\epsilon$-t-butyloxycarbonyl-L-tryptophan.

The conditions employed in the sequence of deprotection, neutralization, coupling, and recoupling for the introduction of each amino acid into the peptide were virtually identical to those of Example 2. A variation occurred in the cleavage reaction of step (2) in which a mixture of 28.8% trifluoroacetic acid, 47.9% chloroform, 5.8% triethylsilane, and 17.5% methylene chloride was employed.

The amino acid analysis of the resulting product gave the following results, lysine being employed as standard: Asn, 1.18; 2Thr, 2.50; Ser, 1.28; Gly, 1.33; Ala, 1.38; 2Phe, 2.16; 2Lys, 2.00; Cha, 1.21; Trp, 0.85. The presence of cysteine was not determined since it is destroyed by the method of analysis.

EXAMPLE 6

L-ALANYL-GLYCYL-L-CYSTEINYL-L-LYSYL-L-ASPARAGINYL-L-PHENYLALANYL-L-PHENYLALANYL-L-TRYPTOPHYL-L-LYSYL-L-THREONYL-L-CYCLOHEXYLALANYL-L-THREONYL-L-SERYL-L-CYSTEINE

The title compound was prepared in accordance with the method of Example 3 using 2.851 grams (at substitution level of 9.148 mmole/gram of the product from Example 5. Purification of the product was accomplished by chromatography on a Sephadex G-25 F column. The chromatographic conditions were: solvent, degassed 0.2 acetic acid; column size, 7.5 × 150 cm.; temperature, 26° C.; flow rate, 650 ml./hour; fraction volume, 22.75 ml.

Absorbance at 280 mμ of each fraction plotted versus fraction number indicated one large peak with trailing impurities. A collection of two sets of fractions was made. The fractions which were combined and their effluent volumes are as follows:

Fractions 195-209 (4413-4755 ml.)
Fractions 210-227 (4756-5164 ml. )

UV spectroscopy indicated that the second sample showing a theoretical amount of 305.4 mg. was the better product. An Ellman titration of an aliquot indicated a free sulfhydryl content of 96% of theoretical.

EXAMPLE 7

OXIDATION TO L-Cha[11]-SOMATOSTATIN

The reduced L-Cha[11]-somatostatin from Example 6 was treated according to the method of Example 4. The product was absorbed on a Sephadex G-25 F column. The chromatographic conditions were as follows: solvent, degassed 50% acetic acid; column size, 5.0 × 90 cm.; temperature, 26° C.; flow rate, 276 ml./hour; fraction volume, 16.1 ml.

Absorbance of 280 mµ for each fraction plotted versus fraction number indicated two large peaks. The first peak represented aggregated forms of the product, and the second peak represented good monomeric product. The product represented by the second peak was collected and lyophilized to dryness. The resulting white solid was dissolved in 15 ml. of degassed 0.2 M acetic acid, and the solution was applied to a Sephadex G-25 F column. The chromatographic conditions were: solvent, degassed 0.2 M acetic acid; column size, 5.0 × 150 cm.; temperature, 26° C.; flow rate, 486 ml/hour; fraction volume, 17 ml.

Absorbance at 280 mµ of each fraction plotted versus fraction number indicated one large peak. UV spectroscopy troscopy showed the large peak to be good product. Fractions 151–162 (effluent volumes of 2550–2754 ml.) were combined and lyophilized to dryness in the dark to obtain 136.7 mg. of the desired product.

Optical rotation $[\alpha]_D^{26} = -44.7°$ (1 percent acetic acid).

Amino acid analysis: Ala, 1.01; Gly, 0.99; 2Cys, 2.10; 2Lys, 1.96; Asn, 1.02; 2Phe, 1.73; Trp, 0.91; 2Thr, 1.94; Cha, 1.07; Ser, 0.77.

The above results are expressed as ratios to one-half the sum of glycine and alanine. Cysteine was determined as cysteic acid from hydrolysis in the presence of dimethyl sulfoxide; tryptophan was determined from hydrolysis in the presence of thioglycolic acid; serine was not corrected for losses during hydrolysis.

EXAMPLE 8

N-t-BUTYLOXYCARBONYL-L-ALANYL-GLYCYL-L-(S-p-METHOXYBENZYL)CYSTEINYL-L-(N$^\epsilon$-o-CHLOROBENZYLOXYCARBONYL)LYSYL-L-ASPARAGINYL-L-PHENYLALANYL-L-PHENYLALANYL-L-TRYPTOPHYL-L-(N$^\epsilon$-o-CHLOROBENZYLOXYCARBONYL)LYSYL-L-(O-BENZYL)THREONYL-L-LEUCYL-L-(O-BENZYL)THREONYL-L-(O-BENZYL)SERYL-L-(S-p-METHOXYBENZYL)CYSTEINYL METHYLATED POLYSTYRENE RESIN This compound was prepared by a method similar to that described in Example 2 and using 3.5 grams of the product from Example 1 as starting material. The Beckman 990 automatic peptide synthesizer was used for the entire sequence. N-t-Butyloxycarbonyl-L-leucine was used in place of N-t-butyloxycarbonyl-D-phenylalanine. The conditions employed in the sequence of deprotection, neutralization, coupling, and recoupling for the introduction of each amino acid into the peptide were virtually identical to those of Example 2. A variation occurred in the cleavage reaction of step (2) in which a mixture of 28.8% trifluoroacetic acid, 47.9% chloroform, 5.8% triethylsilane, and 17.5% methylene chloride was employed.

The amino acid analysis of the resulting product gave the following results, lysine being employed as standard: Ala, 1.41; Gly, 1.26; 2Lys, 2.0; Asn, 1.20; 2Phe, 2.16; Trp, 0.82; 2Thr, 2,38; Leu, 1.15; Ser, 1.18. The presence of cysteine was not determined since it is destroyed by the method of analysis.

EXAMPLE 9

L-ALANYL-GLYCYL-L-CYSTEINYL-L-LYSYL-L-ASPARAGINYL-L-PHENYLALANYL-L-PHENYLALANYL-L-TRYPTOPHYL-L-LYSYL-L-THREONYL-L-LEUCYL-L-THREONYL-L-SERYL-L-CYSTEINE

The title compound was prepared in accordance with the method of Example 3 using 2.875 grams (at substitution level of 0.152 mmole/gram resin) of the product from Example 8. Purification of the product was accomplished by chromatography on a Sephadex G-25 F column. The chromatographic conditions were: solvent, degassed 0.2 M acetic acid; column size, 7.5 × 150 cm.; temperature, 26° C.; flow rate, 666 ml./hour; fraction volume, 23.3 ml.

Absorbance at 280 mµ of each fraction plotted versus fraction number indicated one very large peak with low, broad, leading and trailing shoulders. A collection of three sets of fractions was made. The fractions which were combined and their effluent volumes are as follows:

Fractions 180–196 (4163–4560 ml.)
Fractions 197–215 (4561–5003 ml.)
Fractions 216–275 (5004–6405 ml.)

UV spectroscopy indicated that the second sample showing a theoretical amount of 320 mg. was the best product. An Ellman titration of an aliquot indicated a free sulfhydryl content of 88.5% of theoretical.

EXAMPLE 10

OXIDATION TO L-Leu[11]-SOMATOSTATIN

The reduced L-Leu[11]-somatostatin from Example 9 was treated according to the method of Example 4. The product was absorbed on a Sephadex G-25 F column. The chromatographic conditions were as follows: solvent, degassed 50% acetic acid; column size, 5.0 × 90 cm.; temperature, 26° C.; flow rate, 282 ml./hour; fraction volume, 16.3 ml.

Absorbance at 280 mµ for each fraction plotted versus fraction number indicated two large peaks. The first peak represented aggregated forms of the product, and the second peak represented good monomeric product. The product represented by the second peak was collected, combined with the corresponding material from another preparation, and the total was lyophilized to dryness. The solid was dissolved in 10 ml. of degassed 0.2 M acetic acid, and the solution was applied to a Sephadex G-25 F column. The chromatographic conditions were: solvent, degassed 0.2 M acetic acid; column size, 5.0 × 150 cm.; temperature, 26° C.; flow rate, 498 ml./hour; fraction volume, 17.5 ml.

Absorbance at 280 mµ of each fraction plotted versus fraction number indicated one large peak with a small leading shoulder. UV spectroscopy showed the large peak to be good product. Fractions 139–153 (effluent volumes of 2421–2686 ml.) were combined and lyophilized to dryness in the dark to obtain 130.8 mg. of the desired product.

Optical rotation $[\alpha]_D^{26} = -28.1°$ (1 percent acetic acid).

Amino acid analysis: Ala, 1.03; Gly, 0.97; 2Cys, 1.83; 2Lys, 1.96; Asn, 0.94; 2Phe, 1.95; Trp, 0.89; 2Thr, 1.83; Leu, 0.95; Ser, 0.83.

The above results are expressed as ratios to onehalf the sum of glycine and alanine. Cysteine was determined as cysteic acid from hydrolysis in the presence of dimethyl sulfoxide; tryptophan was determined from hydrolysis in the presence of thioglycolic acid; serine was not corrected for losses during hydrolysis.

D-Phe[11]-somatostatin, L-Cha[11]-somatostatin, and L-Leu[11]-somatostatin were tested for their activity in inhibiting gastric acid secretion. Large 5–6 inch bullfrogs were pithed. The gastric mucosa was freed from the muscle layers and was bisected logitudinally. The two halves were mounted in separate acrylic plastic chambers. The secretory area which was exposed was 2.85 square centimeters, and the volume of each half of the chamber was 5 ml. The solutions which were used to bathe the mucosa were the same as those used by Durbin et al., *Biochemica et Biophysics Acta*, 321, 553–560 (1973), with the exception that the serosal fluid contained sodium dihydrogen phosphate at a 1 millimolar concentration. Both sides of the chamber were aerated with a mixture of 95% oxygen and 5% carbon dioxide. The acid secretory rate was followed by maintaining the secretory solution at a pH of 4.5.

A concentration of $1 \times 10^{-5}$ moles per liter of pentagastrin was used on the serosal side of the tissue to stimulate the acid secretory response. The serosal fluid was renewed every 40 minutes to prevent lowering of pentagastrin concentration by enzymatic hydrolysis of the peptide bonds. Addition of the compound to be tested was done by placing it in the serosal fluid each time the bathing solution was changed.

Spontaneous acid outputs for pentagastrin-stimulated secretion producing no less than 8 microequivalents/hour of acid served as controls. The effect of inhibition of gastric acid secretion was expressed as percent of inhibition from the control periods preceding the introduction of the test compound into the serosal buffer. Only one of the halves of the gastric mucosa was treated with the test compound, the other half serving as control to ensure continued viability of the tissue. After establishing steady state secretion, the test compound was added to the nutrient solution in an amount sufficient to attain an inhibitor concentration of $1 \times 10^{-5}$ moles/liter. The acid was continually titrated to pH 4.5, and the volume of 12.5 mM sodium hydroxide utilized each 20 minutes was used to determine the acid secretory rate. The results were expressed as micro equivalents of acid secreted per hour.

Using this method of evaluation, somatostatin itself produced a percent inhibition of gastric acid secretion of 54.64 plus or minus 6.05 standard error of mean. D-Phe[11]-somatostatin produced a percent inhibition of gastric acid secretion of 53.57 plus or minus 7.32 standard error or mean. L-Cha[11]-somatostatin produced a percent inhibition of gastric acid secretion of 81.83 plus or minus 7.88 standard error of mean. L-Leu[11]-somatostatin produced a percent inhibition of gastric acid secretion of 45.38 plus or minus 11.70 standard error of mean.

D-Phe[11]-somatostatin and L-Cha[11]-somatostatin also were tested in dogs for their in vivo inhibition of gastric acid secretion. In six dogs with chronic fistula and Heidenhain pouch, gastric HCl secretion was induced by infusion of the C-terminal tetrapeptide of gastrin at 0.5 µg/kg-hr. One dog served as control, receiving only the tetrapeptide. Another dog received the tetrapeptide and somatostatin while the test compound was administered to the remaining dogs in place of somatostatin. After one hour of steady state secretion of HCl, somatostatin or the test compound was infused at 3 µg/kg-hr. for one hour. Collection of gastric acid samples was continued for an additional 1.5 hours at 15 minute intervals. The samples were titrated to pH 7 with an automatic titrator. The maximal inhibitory effect of the test compounds was extrapolated against the dose-response curve of somatostatin, and the relative potency of the analogs to that of somatostatin is expressed as percent activity. D-Phe[11]-somatostatin inhibited steady state acid secretion induced by the C-terminal tetrapeptide of gastrin by 32.19 plus or minus 6.55% standard error of mean. This effect is equivalent to that of 0.086 µg/kg-hr. of somatostatin. Its activity relative to that of somatostatin thus is 2.87%. L-Cha[11]-somatostatin inhibited steady state acid secretion induced by the C-terminal tetrapeptide of gastrin by 31.37 plus or minus 4.08% standard error of mean. This effect is equivalent to that of 0.0825 µg/kg-hr. of somatostatin. Its activity relative to that of somatostatin therefore is 2.7%.

D-Phe[11]-somatostatin, L-Cha[11]-somatostatin, and L-Leu[11]-somatostatin also were tested for their activity with respect to the release of growth hormone. The procedure which was employed is carried out using mature male Spraque-Dawley rats (Laboratory Supply Company, Indianapolis, Indiana). The test is a modification of the method of P. Brazeau, W. Vale, and R. Guilleman, *Endocrinology*, 94 184 (1974). In each assay, a set comprising three groups of eight rats each was employed. First, sodium pentobarbital was administered to all of the rats of the particular set to stimulate growth hormone secretion. In each set, one group served as control group and received only saline. A second group received somatostatin at 50 µg./rat, subcutaneously. The third group received test compound at 50 µg./rat, subcutaneously. The degree of inhibition of serum growth hormone concentration then was determined with respect to the control group, and the relative activities of test compound and somatostatin itself were compared.

From the above assay, the following results were obtained:

D-Phe[11]-somatostatin inhibited the increase in serum growth hormone concentration by 70% over control compared to 57% for somatostatin.

L-Cha[11]-somatostatin inhibited the increase in serum growth hormone concentration by 33% over control compared to 73% for somatostatin.

L-Leu[11]-somatostatin inhibited the increase in serum growth hormone concentration by 22% over control compared to 87% for somatostatin.

The tetradecapeptides were tested for their in vivo activity in inhibiting glucagon and insulin secretion upon stimulation with L-alanine. Normal mongrel dogs of either sex were fasted overnight. Control blood samples were obtained, and then an intravenous infusion of saline, somatostatin, or test compound was started. After 30 minutes, L-alanine additionally was administered intravenously for a period of 15 minutes. The infusion of saline, somatostatin, or test compound was continued for 15 minutes after completion of the alanine infusion. The total dose of somatostatin or test compound which was infused is 200–500 µg/dog (about 0.20–0.30 µg/kg./minute), and the total dose of L-alanine infused was 1 mmol/kg. The infusion of L-alanine produced an abrupt increase in the serum concentration of glucagon and insulin. This returned to control concentration when the alanine infusion was discontinued.

Somatostatin infusion caused a decrease in basal serum insulin concentration and inhibited the rise in concentration of both glucagon and insulin during the infusion of L-alanine. In comparison, the D-Phe[11]-somatostatin, infused at a rate of 0.211 μg/kg/min., did not affect the increase in serum glucagon concentration and serum insulin concentration produced by the infusion of L-alanine.

L-Cha[11]-somatostatin, infused at a rate of 0.235 μg/kg/min., caused a decrease in the basal serum concentration of both insulin and glucagon, but it did not inhibit the increase in serum concentration of either hormone which results from infusion of L-alanine. L-Leu[11]-somatostatin, infused at a rate of 0.195 μg/kg/min., had no affect on the basal serum concentration of either insulin or glucagon, had no effect on the increase in glucagon concentration produced by L-alanine, and caused only a partial inhibition of the increase in insulin secretion produced by L-alanine infusion.

The tetradecapeptides also were evaluated for in vivo activity in inhibiting glucagon secretion upon stimulation with insulin. Normal mongrel dogs of either sex were fasted overnight. After control blood samples had been obtained, an intravenous infusion of saline, somatostatin, or the test compound was commenced. After 15 minutes, insulin, 0.3 units/kg., was injected intravenously. The infusion of saline, somatostatin, or the test compound was continued for two hours, and blood samples were obtained at various intervals throughout the test. The total dose of the somatostatin or test compound ranged from 120–260 μg./dog (0.07–0.13 μg/kg/min.). Administration of insulin produced a reduction in the blood glucose concentration and an increase in serum glucagon concentration. Infusion of somatostatin blocked the increase in serum glucagon concentration but had no effect on the reduction of the blood glucose concentration.

In comparison, when, instead of somatostatin, D-Phe[11]-somatostatin was infused at a rate of 0.128 μg/kg/min. L-Cha[11]-somatostatin was infused at a rate of 0.130 μg/kg/min., or L-Leu[11]-somatostatin was infused at a rate of 0.129 μg/kg/min., it was found that none of these compounds inhibited the increase in serum glucagon concentration produced by insulin administration.

I claim:

1. A compound selected from those of the formula

H-L-Ala-Gly-L-Cys-L-Lys-L-
Asn-L-Phe-L-Phe-L-Trp-L-Lys-L-Thr-Y-L-Thr-L-Ser-L-Cys-OH and their pharmaceutically acceptable non-toxic acid addition salts, and R-L-Ala-Gly-L-Cys(R$_1$)-L-Lys(R$_2$)-L-Asn-L-Phe-L-Phe-L-Trp(R$_5$)-L-Lys(R$_2$)-L-Thr(R$_3$)-Y-L-Thr(R$_3$)-L-Ser(R$_4$)-L-Cys(R$_1$)-X; in which Y is D-Phe, L-Cha, or L-Leu;
R is hydrogen or an α-amino protecting group;
R$_1$ is hydrogen or a thio protecting group;
R$_2$ is hydrogen or an E-amino protecting group;
R$_3$ and R$_4$ each are hydrogen or a hydroxy protecting group;
R$_5$ is hydrogen or formyl; and
X is hydroxy or

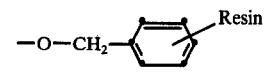

in which the resin is polystyrene; with the proviso that, when X is hydroxy, each of R, R$_1$, R$_2$, R$_3$, R$_4$, and R$_5$ is hydrogen, and, when X is

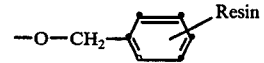

each of R, R$_1$, R$_2$, R$_3$, and R$_4$ is other than hydrogen.

2. Compound of claim 1, having the formula

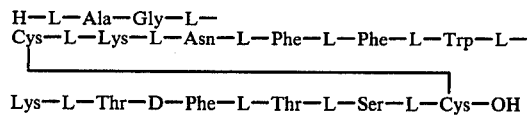

and pharmaceutically acceptable non-toxic acid addition salts thereof.

3. Compound of claim 1, having the formula R-L-Ala-Gly-L-Cys(R$_1$)-L-Lys(R$_2$)-L-Asn-L-Phe-L-Phe-L-Trp(R$_5$)-L-Lys(R$_2$)-L-Thr(R$_3$)-D-Phe-L-Thr(R$_3$)-L-Ser(R$_4$)-L-Cys(R$_1$)-X.

4. Compound of claim 3, in which X is hydroxy.

5. Compound of claim 3, in which X is

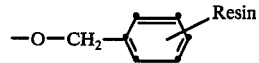

6. Compound of claim 5, in which R is t-butyloxycarbonyl.

7. Compound of claim 5, in which R$_1$ is p-methoxybenzyl.

8. Compound of claim 5, in which R$_2$ is o-chlorobenzyloxycarbonyl.

9. Compound of claim 5, in which R$_3$ and R$_4$ are benzyl.

10. Compound of claim 5, having the formula

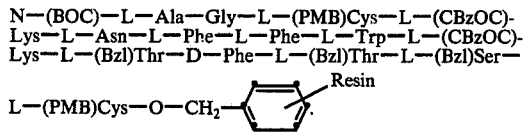

11. Compound of claim 1, having the formula

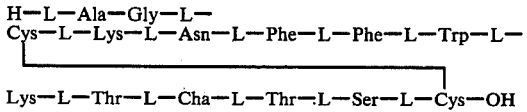

and pharmaceutically acceptable non-toxic acid addition salts thereof.

12. Compound of claim 1, having the formula R-L-Ala-Gly-L-Cys(R$_1$)-L-Lys(R$_2$)-L-Asn-L-Phe-L-Phe-L-Trp(R$_5$)-L-Lys(R$_2$)-L-Thr(R$_3$)-L-Cha-L-Thr(R$_3$)-L-Ser(R$_4$)-L-Cys(R$_1$)-X.

13. Compound of claim 12, in which X is hydroxy.

14. Compound of claim 12, in which X is

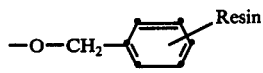

15. Compound of claim 14, in which R is t-butyloxycarbonyl.

16. Compound of claim 14, in which $R_1$ is p-methoxybenzyl.

17. Compound of claim 14, in which $R_2$ is o-chlorobenzyloxycarbonyl.

18. Compound of claim 14, in which $R_3$ and $R_4$ are benzyl.

19. Compound of claim 14, having the formula

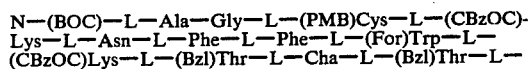
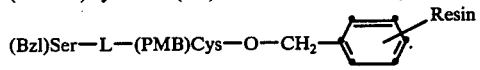

20. Compound of claim 1, having the formula

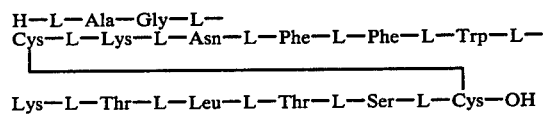

and pharmaceutically acceptable non-toxic acid addition salts thereof.

21. Compound of claim 1, having the formula R-L-Ala-Gly-L-Cys($R_1$)-L-Lys($R_2$)-L-Asn-L-Phe-L-Phe-L-Trp($R_5$)-L-Lys($R_2$)-L-Thr($R_3$)-L-Leu-L-Thr($R_3$)-L-Ser($R_4$)-L-Cys($R_1$)-X.

22. Compound of claim 21, in which X is hydroxy.

23. Compound of claim 21, in which X is

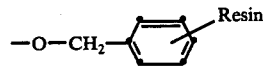

24. Compound of claim 23, in which R is t-butyloxycarbonyl.

25. Compound of claim 23, in which $R_1$ is p-methoxybenzyl.

26. Compound of claim 23, in which $R_2$ is o-chlorobenzyloxycarbonyl.

27. Compound of claim 23, in which $R_3$ and $R_4$ are benzyl.

28. Compound of claim 23, having the formula

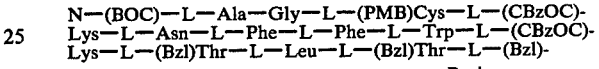
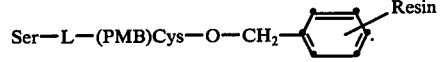

* * * * *

UNITED STATES PATENT AND TRADEMARK OFFICE
CERTIFICATE OF CORRECTION

PATENT NO. : 4,061,607
DATED : December 6, 1977
INVENTOR(S) : James E. Shields

It is certified that error appears in the above-identified patent and that said Letters Patent are hereby corrected as shown below:

Column 3, line 29, "cysteine ora" should read --cysteine or a--.

Column 12, line 50, "9.148 mmole/gram" should read --0.148 mmole/gram)--.

Column 13, line 25, "copy troscopy showed" should read --copy showed--.

Column 14, line 1, "2,38;" should read --2.38;--.

Column 17, line 66, "E-amino" should read --$\varepsilon$-amino--.

Signed and Sealed this

Twentieth Day of February 1979

[SEAL]

Attest:

RUTH C. MASON
*Attesting Officer*

DONALD W. BANNER
*Commissioner of Patents and Trademarks*